United States Patent [19] [11] 4,283,553
Ivanchev et al. [45] Aug. 11, 1981

[54] HYDROPEROXIDE DERIVATIVES OF HYDROXYETHYLATED COMPOUNDS AND METHOD OF PRODUCING SAME

[76] Inventors: Sergei S. Ivanchev, ulitsa Nalichnaya, 36/3, kv. 97; Anatoly A. Syrov, ulitsa III Internatsionala, 52, kv. 51; Valery N. Pavljuchenko, prospekt Energetikov, 34, kv. 53; Ninel N. Lesnikova, ulitsa Vernosti, 20, kv. 1; Diana A. Rozhkova, prospekt Metalistov, 8, kv. 77, all of Leningrad, U.S.S.R.

[21] Appl. No.: 78,037

[22] Filed: Sep. 24, 1979

[51] Int. Cl.³ .................. C07C 69/66; C07C 43/11; C07C 179/025
[52] U.S. Cl. ..................... 560/176; 260/404; 560/112; 560/122; 568/497; 568/567; 568/568
[58] Field of Search ............. 568/567, 568, 497; 560/122, 176, 112, 600; 260/404

[56] References Cited

U.S. PATENT DOCUMENTS

| | | | |
|---|---|---|---|
| 2,973,372 | 2/1961 | Thompson | 568/568 |
| 3,022,352 | 2/1962 | Milas | 560/112 |
| 3,236,872 | 2/1966 | Manly | 568/567 |
| 3,399,219 | 8/1968 | Braunwarth | 560/176 |
| 3,939,138 | 2/1976 | Suzuki et al. | 252/415 |
| 4,158,021 | 6/1979 | Roskott | 568/567 |

FOREIGN PATENT DOCUMENTS 889652  2/1962  United Kingdom ............. 568/568

OTHER PUBLICATIONS

Silbert "J. Amer. Chem. Soc." Oct. 1962, vol. 39, No. 11, pp. 480–487.
Coleman, Journal of The American Chemical Society, pp. 4886–4889, vol. 74, No. 19 (1952).
King, Journal of The Chemical Society, pp. 587–593, (1956).

Primary Examiner—Werren B. Lone
Attorney, Agent, or Firm—Lackenbach, Lilling & Siegel

[57] ABSTRACT

Disclosed are novel hydroperoxide derivatives of hydroxyethylated compounds of the general formula:

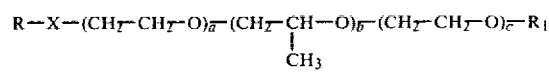

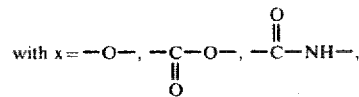

a-whole number 10 to 30, b, c are absent, $R = $ n-alkyl from $C_8$ to $C_{20}$, secondary alkyl of $C_{14}$, $C_{15}$ and

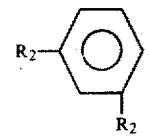

where $R_2 = $ n-alkyl from $C_8$ to $C_{12}$

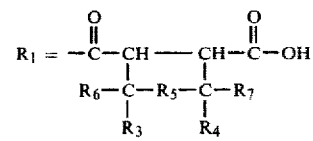

where $R_3$ and $R_4 = R_8$—C=O, where $R_8 = $—$CH_3$ or H, if $R_{6,7,9} = H$ $R_5$ is absent or

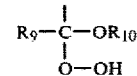

where $R_9 = $—$CH_3$ or H, if $R_{6,7,8} = H$, $R_5$ is absent; $R_{10} = $ n-alkyl of $C_1$ to $C_9$ of $R_3 \neq R_4$ $R_5 = $—$CH_2$ if $R_{6,7,8,9} = H$; if $R_5$ is absent, $R_1$ is acyclic and is

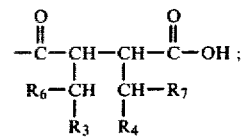

$R_6 = $—$CH_3$ or H, if $R_{7,8,9} = H$, $R_5$ is absent, $R_7 = $—$CH_3$ or H, if $R_{6,8,9} = H$, $R_5$ is absent, with $x = $—O—, b-whole number of 8 to 24, (a+c)-whole number of 6 to 30

$R = R_1$

According to the invention, a method of producing novel hydroperoxide derivatives of hydroxyethylated compounds resides in that certain hydroxyethylated compounds are caused to interact with specific derivatives of dienes and maleic anhydride followed by ozonization of the resulting product.

8 Claims, No Drawings

HYDROPEROXIDE DERIVATIVES OF HYDROXYETHYLATED COMPOUNDS AND METHOD OF PRODUCING SAME

The invention relates to novel organic surface-active compounds, and more particularly to hydroperoxide derivatives of hydroxyethylated compounds, methods of producing same, and their use as initiators of emulsion polymerization and as emulsion stabilizers.

The proposed novel compounds, namely hydroperoxide derivatives of hydroxyethylated compounds, can be used as initiators for a variety of processes proceeding according to a radical mechanism, the processes can be carried out both in aqueous and organic media owing to solubility of said compounds both in water and in organic solvents.

Concurrent with the ability to generate, at elevated temperatures, free radicals, the hydroperoxide derivatives of hydroxyethylated compounds exhibit pronounced surface-active properties.

The combination of said properties makes it possible to employ hydroperoxide derivatives of hydroxyethylated compounds for initiating the radical processes proceeding in emulsions, said compounds therewith function simultaneously as emulsion stabilizers. Hydroperoxide derivatives of hydroxyethylated compounds can have the best practical significance when used for initiating the emulsion polymerization of vinyl monomers and stabilizing the latexes formed. Due to chemical bonding of the emulsifier with the surface of latex particles, the latexes obtained in the presence of hydroperoxide derivatives of hydroxyethylated compounds enjoy improved stability.

The proposed hydroperoxide derivatives of hydroxyethylated compounds can be used for carrying out reactions of emulsion polymerization with a monomer to water ratio of from 1:1 to 1:10, thus providing the emulsion stabilization and, at the same time, the generation of free radicals at rather low temperatures (40°–80° C.), with the concentration of the hydroperoxide derivatives of hydroxyethylated compounds making up from 2 to 10 percent of the monomer mass.

Unlike all known surface-active substances, the proposed hydroperoxide derivatives of hydroxyethylated compounds are substantially emulsifiers of a mixed type, i.e. they combine properties of both ionic and non-ionic surface-active substances.

Said feature permits their use as emulsifiers over a wide range of medium pH (5–11) at rather low concentrations (2 percent with respect to the monomer mass).

The hydroperoxide derivatives of hydroxyethylated compounds can also be used in combination with conventional emulsifiers to carry out emulsion polymerization, in an amount of from $10^{-2}$–$10^{-4}$ percent of the monomer mass, which is by 1–3 orders less than the concentration of conventional initiators.

As monomers styrene, butadiene and its derivatives, derivatives of acrylic and methacrylic acids, and other monomers can be used. The hydroperoxide derivatives can also be used to initiate graft-copolymerization of vinyl monomers and the diene-type elastomers when producing shockproof copolymers, for example ABS-plastics.

The implementation of a copolymerization process at said concentrations of hydroperoxide derivatives of hydroxyethylated compounds permits to synthesizing polymers practically free from the initiator residues, which can be favorable to the production of light- and weather-resistant materials. Moreover, the extremely low concentrations of the initiator enable to obtaining extraordinarily high polymers (of molecular mass over $10^7$) enjoying radically new properties. For example, polystyrene of such a high molecular mass becomes shockproof. It should be also noted, that the polymeric dispersions obtained in the presence of the hydroperoxide derivatives of hydroxyethylated compounds exhibit resistance to electrolytic exposure and mechanical action as well.

With their novelty, the proposed compounds have no analogues in the prior art disclosed.

According to the invention, the hydroperoxide derivatives of hydroxyethylated compounds are those of the formula:

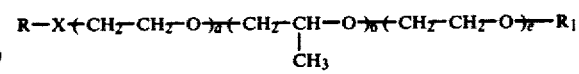

with $x = -O-$,

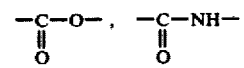

a—whole number from 10 to 30; b,c are absent;
R = n-alkyl from $C_8$ to $C_{20}$, secondary alkyl $C_{14}$, $C_{15}$,

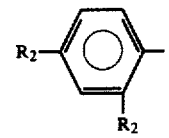

where $R_2$ = n-alkyl from $C_8$ to $C_{12}$;

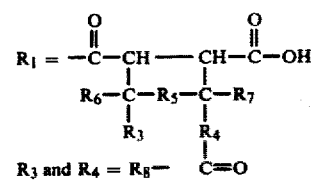

where
where $R_8 = -CH_3$ or H with $R_{6,7,9} = H$ $R_5$ is absent, or

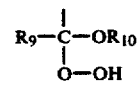

where $R_9 = -CH_3$ or H with $R_{6,7,8} = H$; if $R_5$ is absent, $R_1$ is acyclic and is

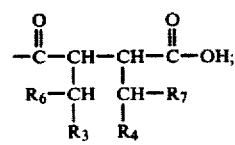

$R_5$ is absent;

$R_{10}$=n-alkyl of $C_1$ to $C_9$ if $R_3 \neq R_4$;
$R_5$=—$CH_2$—with $R_{6,7,8,9}$=H
$R_6$=—$CH_3$ or H with $R_{7,8,9}$=H $R_5$ is absent,
$R_7$=—$CH_3$ or H with $R_{6,8,9}$=H $R_5$ is absent,
with X=—O—, b—whole number from 8 to 24, (a+c)—whole number from 6 to 30, $$R = R_1$$

Said novel compounds are substantially surface-active agents comprising reactive functional groups capable of participating in radical reactions of polymerization.

Hydroperoxide derivatives of hydroxyethylated compounds constitute anionic-nonionic type emulsifiers since they combine in their structure a polyoxyethylene chain and a carboxy group capable of dissociation. Therefore, physical and chemical properties of these compounds depend, to a great extent, on the medium pH-value.

0.01 g of said substance dissolved in 100 g of water decreases the surface tension to 39–50 dynes/cm.

By the critical concentration of produced the micellar mass, the compounds obtained are close to nonionic surface-active substances. The critical concentration of micelle-formation is in the range from 0.003 g/l to 0.03 g/l.

The micellar mass varies from 240 000 to 140 000.

Hydroperoxide derivatives of hydroxyethylated compounds can be used over a wide temperature range, since the fogging temperature at pH of 5.8 is 100° C.

Hydroperoxidic derivatives of hydroxyethylated compounds are explosion-proof even upon rapid heating up to 300° C., decomposition occurs with no explosion. Thus there is no danger when handling them.

Identification of the end products is carried out according to the following factors:

a. elementary analysis for carbon and hydrogen;
b. determination of the acid number;
c. analysis for the active oxygen content by iodometric technique based on the interaction of hydroperoxides and $SO_2$;
d. attribution of the functional groups detected in IR-spectra of the resulting products: carbonyl groups at 1740 $cm^{-1}$;
e. determination of molecular mass by measuring the condensation heats;

The molecular mass of polymers was determined by viscometry with the use of values of the constants K and α in the Marc Howvink equation $$[\eta] = KM^\alpha;$$

for polysterene, $K=2.7\times 10^{-4}$ and $\alpha=0.66$ (25° C., benzene as a solvent);
for polymethyl methacrylate $K=0.468\times 10^{-4}$ and $\alpha=0.77$ (25° C., benzene);
for polybutyl acrylate $K=6.85\times 10^{-3}$ and $\alpha=0.75$ (25° C., acetone);
for polychloroprene $K=2.02\times 10^{-3}$ and $\alpha=0.89$ (25° C., benzene).

The size of the latex particles was determined by the light scattering method or by electronic microscopy.

Hydroperoxide derivatives of hydroxyethylated compounds are of interest as surface-active agents to be used as emulsifiers in the processes of emulsion polymerization of vinyl polymers and as initiators.

As emulsifiers, they ensure stability of the monomer's initial emulsion and resulting polymer dispersion.

As a result of the monomer emulsification in the presence of surface-active agents, at least two zones of dispersion are formed, namely a zone of coarse disintegration (drops of the monomer) corresponding to a regular emulsion, and a zone of colloid dispersion associated with micelle-formation and accumulation of the monomer in the emulsifier micelles due to solubilization.

Surface-active agents are among the major components responsible for the course of emulsion polymerization processes.

If, due to some factors or actions (temperature, addition of electrolyte, etc.), the colloid state of the emulsifier is changed, the kinetics of the emulsion polymerization and dispersity of the resulting latex are changed respectively.

The kinetics and topochemistry of the emulsion polymerization depend also on the character and concentration of the emulsifier.

Hydroperoxide derivatives of hydroxyethylated compounds are substantially emulsifiers having reactive functional groups capable of participating in the radical reactions of polymerization.

In case of uniform distribution of such an emulsifier in the system, localization of free-radical chemical reactions in the zone of adsorptive layers may occur. By practicing such reactions, one can find an approach to control elementary reactions of polymerization and to obtain polymers having novel properties, for example those of a high molecular mass.

A method for producing hydroperoxide derivatives of hydroxyethylated compounds is also proposed. According to the invention, the method of producing said compounds resides in that hydroxyethylated compounds having an end hydroxyl group of the general formula:

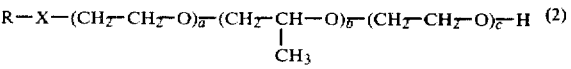

at x=—O—;

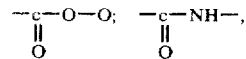

where a—whole number from 10 to 30; b,c—are absent, R=n-alkyl, secondary alkyl $C_{14}$, $C_{15}$,

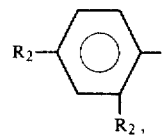

where $R_2$=n-alkyl from $C_8$ to $C_{12}$, at x=—O—; b—whole number from 8 to 24; (a+c)—whole numbers from 6 to 30 are caused to interact with the derivatives of dienes and maleic anhydride of the general formula:

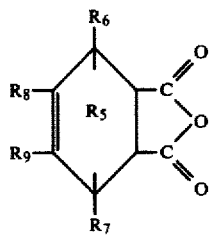

(3)

where
R₆=H; —CH₃;
R₇=H; —CH₃;
R₅=—CH₂— or is absent; if R₅ is absent, the free bonds of the carbon atoms are substituted by hydrogen atoms;
R₈=H; —CH₃;
R₉=H; —CH₃ with subsequent ozonization of the acylate in the medium or in the presence of aliphatic alcohols at a temperature of from −40 to +10° C.

Selected for ozonization are aliphatic alcohols from $C_1$ to $C_9$.

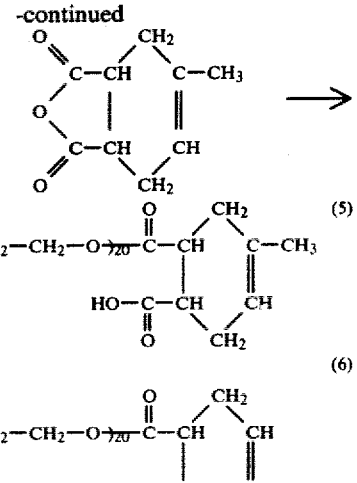

The mixture of the isomers (5) and (6) is then ozonized in the medium of ethyl alcohol.

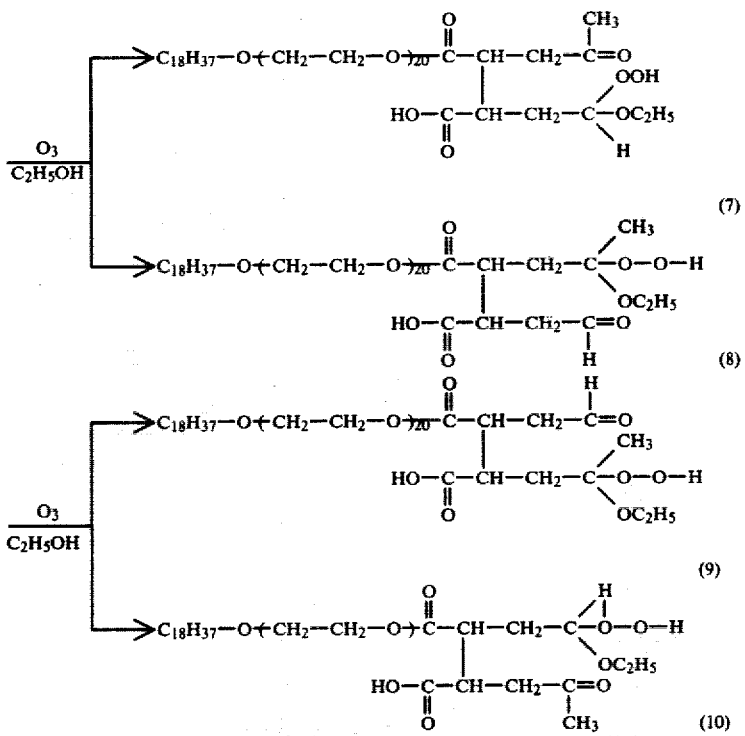

Ozonization is carried out at lowered temperatures to avoid products of a deeper oxidation, which are usually formed at temperatures over +10° C.

The proposed method for producing hydroperoxide derivatives of hydroxyethylated compounds is carried out as follows. The initial products, for example oxyethylated alcohol-octa/declyoxyeicosaethylene oxide and the Diels-Alder adduct, namely 4-methyl-cis-Δ4-tetrahydrophthalic anhydride are introduced into a reactor under stirring. The process proceeds according to the following scheme:

$C_{18}H_{37}$—O⁺(CH₂—CH₂—O)₂₀—H  +  (4)

As will be apparent from the above scheme of the synthesis, the resulting hydroperoxide derivatives of hydroxyethylated compounds constitute a mixture of four isomers.

Acylation of the hydroxyethylated compounds is carried out at temperatures of 60°–100° C., preferably at 80° C., with no solvent, at a molar ratio of hydroxyl to anhydride of 1.0:(1.2–2.0), preferably 1.0:1.5. Excessive anhydride is required to substitute completely the hydroxyl groups of the hydroxyethylated compounds. Acylation is checked for completeness by the acid number of the reaction mixture. To remove the unreacted anhydride, the resulting product is dissolved in water (a 10-30 percent solution is prepared) and the solution is then heated up to 60°-80° C., whereupon it separates into two layers. The acylate sinks into the lower layer whereas the hydrolyzed anhydride occupies the upper layer. Said reaction is carried out repeatedly, the purity of the separated product being checked by means of the acid number and elementary composition. Water from the acylate is removed by means of azeotropic distillation with benzene followed by drying at 50°-70° C. in a vacuum (1-5 torrs).

The acylate obtained is dissolved in aliphatic alcohol or a mixture of alcohol/chloroform (a 10-30 percent solution is prepared) and ozonization is carried out at 0°-10° C. until the ozone absorption ceases. The ozone-containing stream (ozone content of 4-5 percent by volume) is blown through the solution at a rate of 200-500 ml/min. Aliphatic alcohol may be supplied, for example, as methyl, ethyl, n-propyl, or n-nonyl alcohols. Subsequent to the ozonization, the resulting product is separated from the solution by distilling off the alcohol and chloroform at a temperature of 20°-30° C. and a lowered pressure (1-20 torrs). Purity of the product is checked by the active oxygen content and elementary composition.

Hydroperoxide derivatives are advantageous since they improve both process parameters and the properties of the polymers and polymeric dispersions based thereon, as well as obtain polymers enjoying novel properties.

Hydroperoxide derivatives of hydroxyethylated compounds provide initiators of low thermal stability (optimal operating temperature range is within 40°-80° C.). However, they are safe and convenient to handle. In particular, they are explosion-proof, and even upon rapid heating up to 300° C., their decomposition occurs with no explosion. Hydroperoxide derivatives of hydroxyethylated compounds retain their initiating and surface-active properties when stored at temperatures of 0°-10° C. for a long time (at least six months). The temperature of decomposition of hydroperoxide derivatives can be reduced to 0°-5° C. owing to the ability of hydroperoxides to form redox systems in combination with various reducers (salts of metals of variable valence, amines, etc.).

As surface-active initiators, hydroperoxide derivatives of hydroxyethylated compounds are capable of initiating emulsion polymerization and, at the same time, to stabilizing the resulting polymeric dispersions which are resistant, due to the chemical bond of the emulsifier with the polymer, to electrolyte exposure and mechanical actions.

The use of hydroperoxide derivatives of polyalkylene oxides combined with regular emulsifiers as initiators enables emulsion polymerization to be carried out at extremely low concentrations of the initiator $(10^{-2}-10^{-4}\%$ of the monomer mass), thereby providing remarkable high polymers having practically no residual initiator.

Characteristic examples illustrative of the implementation of the method of producing novel compounds, namely hydroperoxide derivatives of hydroxyethylated compounds, are given herein-below.

EXAMPLE 1

48.5 g of octadecyloxyeicosaethylene oxide is fed into a 150 ml reaction vessel provided with a stirrer, a reflux condenser, and a capillary for supplying an inert gas and is then heated up to 80° C.

10.5 g of 4-methyl-cis- $\Delta^4$-tetrahydrophthalic anhydride is added in the melted octadecyloxyeicosyethylene oxide under stirring and the reaction is carried out at 80° C. for five hours in a stream of argon.

Obtained is a mixture of two isomers of acid octadecyloxyeicosasaoxirane-4-methyl-cis- $\Delta^4$-tetrahydrophthalate

and 4-methyl-cis- $\Delta^4$-tetrahydrophthalic anhydride.

The acid number constitutes 80.2 which corresponds to a complete exhaustion of the hydroxyl groups of octadecyloxyeicosaoxirane.

The acylate is dissolved in 250 ml of distilled water, the solution is introduced into a heated separatory funnel and is heated up to 60° C. Upon stratification of the solution, the isomers of the acid octadecyloxyeicosa oxizane 4-methyl-cis - $\Delta^4$-tetrahydrophthalate (the lower layer) are separated followed by fourfold purification according to said technique. The purified product is dried by means of azeotropic distilling of water with benzene followed by drying at 60° C. in vacuum.

The presented structure is supported by the following data: acid number; found 42.6 calculated 42.6; elementary composition: found H—9.5; C—59.7; calculaed H—9.7; C—61.0.

IR-spectrum of the synthesized substance reveals absorption in the band of 1740 cm$^{-1}$, which is characteristic of carbonyl groups.

The yield of the isomers of acid octadecyloxyeicosaoxirane 4-methyl-cis $\Delta^4$-tetrahydrophthalate is 64% (relative to octadecyloxyeicosaoxirane).

30 g of the isomers of acid octadecyloxyeicosaoxirane 4-methyl-cis- $\Delta^4$-tetrahydrophthalate was dissolved in 200 ml of ethyl alcohol, whereupon ozonization was carried out at 0° C. and at a rate of the ozone-containing flow of 300 ml/min until the absorption of ozone was ceased.

Subsequent to ozonization, ethyl alcohol was distilled off at 25° C. and at a lowered pressure.

Obtained is a mixture of four isomers of hydroperoxide derivatives of octadecyloxyeicosaoxirane.

1. 2-formyl-methyl-3-carboxy-5-ethoxy-5-hydroperoxyhexanoyloctadecyloxyeicosaethylene oxide.

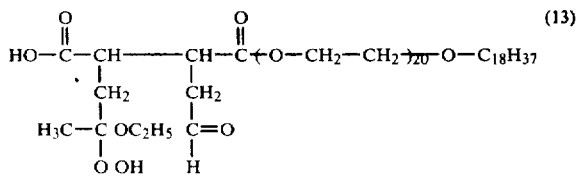

2. 2-(2-ethoxy-2-hydroperoxyethyl)-3-carboxy-5-oxohexanoyloctadecyloxyeicosaethylene oxide

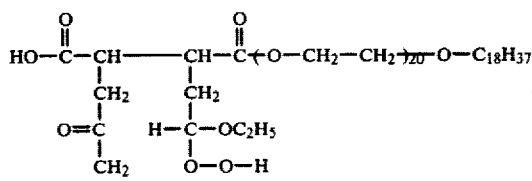

(14)

3. 2-acetonyl-3-carboxy-5-ethoxy-5-hydroperoxypentanoyloxydecyloxyeicosyethylene oxide

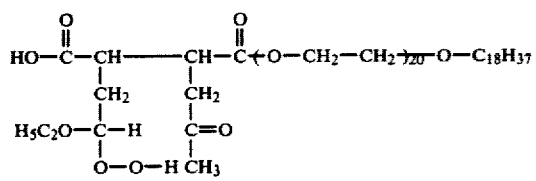

(15)

4. 2-(2-ethoxy-2-hydroperoxypropyl)-3-carboxy-5-oxopentanoyloctadecyloxyeicosaethylene oxide

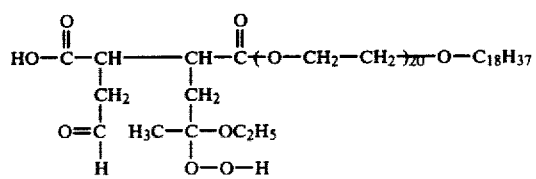

(16)

The presented structures are supported by the following data:
elemental composition, percent: found H—9.3; C—58.5; calculated H—9.5; C—58.7.
active oxygen content, percent: found 1.17; calculated 1.14;
molecular mass: found 1350, calculated 1410.

The resulting hydroperoxide derivatives of the octadecyloxyeicosaethylene oxide exhibit surface-active properties. 0.01 g of the substance dissolved in 100 ml of water resulted in reduction of the surface tension to 44 dynes/cm. The critical level of micelle-formation is 0.0060 g/l.

The yield of hydroperoxide derivatives of the octadecyloxyeicosaethylene oxide is quantitative as related to acid ester.

The hydroperoxide derivatives of octadecyloxyeicosaethylene oxide can be used for emulsion polymerization of styrene.

100 ml of a 2%-solution of hydroperoxide derivatives of octadecyloxyeicosaethylene oxide having pH of 7 and preneutralized with a 2%-solution of sodium hydroxide is fed in a 250 ml reaction vessel provided with a stirrer, a reflux condenser, and a capillary to supply an inert gas. The solution is heated up to 60° C. and then 45 g of styrene is added under stirring. Polymerization is carried out in the stream of argon for two hours. The yield of the polymer provided to be quantitative, the molecular mass being 1,230,000. The resulting latex contains no coagulum and retains, when stored, the aggregative stability for one year at least. The average size of the latex particles is 0.07 μ.

The hydroperoxide derivatives of octadecyloxyeicosaethylene oxide can be used for emulsion polymerization of methyl methacrylate.

Polymerization is carried out in the same way as that of styrene except that methyl methacrylate is substituted for styrene and the process is implemented at a temperature of 40° C. and pH of the aqueous phase of 8.5. In two hours a dispersion with no coagulum is obtained. The yield of the polymer is 98 percent. Molecular mass is 1,400,000. The average diameter of the latex particles is 0.09 μ.

The hydroperoxide derivatives of octadecyloxyeicosaethylene oxide can be also used for emulsion polymerization of n-butyl acrylate.

Polymerization is carried out in the same way as that of methyl methacrylate except that n-butyl acrylate is substituted for methyl methacrylate. The yield of the polymer in 1.5 hours is 96 percent. Molecular mass is 534,000. The average diameter of the rubber particles is 0.10 μ.

The hydroperoxide derivatives of octadecyloxyeicosaethylene oxide can be also used for emulsion graft-copolymerization of styrene.

Copolymerization formulation:
Styrene—60 g
acrylonitrile—20 g
polybutadiene rubber latex—40 g
(dry residue—50 percent, average diameter of the particles 0.165 μ)
emulsifier—potash soap of synthetic fatty acids $C_{10}$—$C_{15}$—1.5 g,
initiator—hydroperoxide derivatives of octadecyloxyeicosaethylene oxide (Example 1) —0.07 g water 280 ml Copolymerization is carried out at 60° C. and pH of the aqueous phase of 10.5 for 100 minutes. In said period, the yield of the copolymer proves to be quantitative.

The hydroperoxide derivatives of octadecyloxyeicosaethylene oxide can be also used for emulsion polymerization of styrene.

Polymerization formulation:
Styrene—90 g
emulsifier—hexa-decyloxyeicosaethylene oxide—4 g,
initiator—hydroperoxide derivatives according to Example 1—0.0015 g,
water—200 ml.

Polymerization is carried out at 50° C. for 9 hours. The polymer yield is 97 percent. Molecular mass is 16,000,000. The impact strength of the polymer is 28 kgf. cm/cm$^2$.

Polystyrene latexes obtained according to this formulation exhibit an elevated resistance both of electrolyte exposure and mechanical actions. Thus, latex obtained according to similar formulation in the presence of a regular initiator exhibits a threshold of coagulation of 1.0 mole/l, whereas a latex synthesized in the presence of hydroperoxide derivatives under said conditions shows no coagulation at all. A 4-hour test of the latex with the Maron instrument brings about no change in the size of the latex particles.

The hydroperoxide derivatives of octadecyloxyeicosaethylene oxide can be also used for emulsion polymerization of chloroprene.

Polymerization formulation:
chloroprene—100 g
emulsifier—hexadecyloxyeicosaethylene oxide—4 g
initiator—hydroperoxide derivatives obtained according to Example 1—0.0029 g
n-dodecyl-mercaptan—1.44 g
water 200 ml Polymerization is carried out at 40° C. for 3 hours. The yield of the polymer is 98 percent. Molecular mass is 600,000. The average diameter of the latex particles is 0.12 μ.

Example 2

The experiment is carried out under conditions similar to those of Example 1 except that 2,4-dinonylphenyloxydecaethylene oxide is substituted for octadecyloxyeicosaethylene oxide.

Molar ratio of the reagents is as described in Example 1.

Acylate separated is substantially a mixture of two isomers of acid 4-methyl-cis- Δ⁴-tetrahydrophthalate of 2,4-dinonylphenyloxydecaethylene oxide.

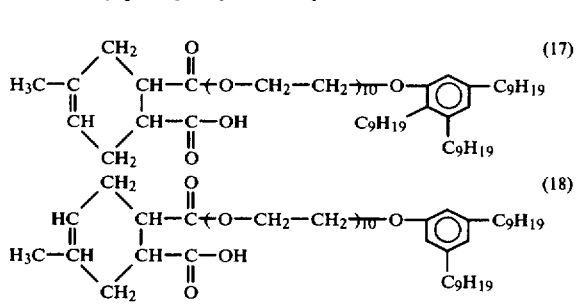

The presented structures are approved by the following data:

acid number: found 58.7; calculated 58.9;

elementary composition, percent; found H 9.7; C 67.0; calculated H 9.7; C 66.8.

IR-spectrum of the substance synthesized reveals absorption in the band of 1740 cm⁻¹, which is characteristic of carbonyl groups.

The yield of acid 2,4-dinonylphenyloxydecaethylene oxide 4-methyl-cis- Δ⁴-tetrahydrophthalate is 75 percent relative to 2,4-dinonylphenyloxydecaethylene oxide.

Ozonization is carried out as in Example 1.

Obtained is a mixture of the following four isomers of hydroperoxide derivatives of 2,4-dinonylphenyloxydecaethylene oxide.

1. 2-formyl-methyl-3-carboxy-5-ethoxy-5-hydroperoxyhexanoyl-2,4-dinonylphenyloxydecaethylene oxide

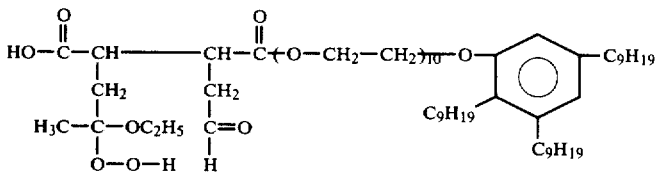

2. 2-(2-ethoxy-2-hydroperoxyethyle)-3-carboxy-5-oxohexanoyl-2,4-dinonylphenyloxydecaethylene oxide

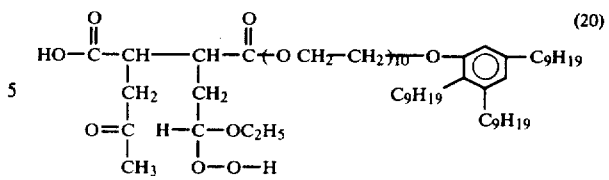

3. 2-acetonyl-3-carboxy-5-ethoxy-5-hydroperoxypentanoyl-2,4-dinonylphenyloxydecaethylene oxide

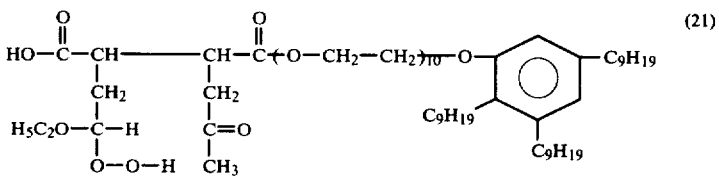

4. 2-(2-ethoxy-2-hydroperoxypropyl)-3-carboxy-5-oxopentanoyl-2,4-dinonylphenyloxydecaethylene oxide

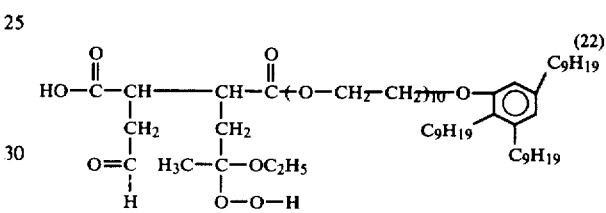

The presented structures are supported by the following data:

elementary composition, percent: found H—9.1; C—63.6; calculated H—9.3; C—63.0;

active oxygen content, percent: found 1.47; calculated 1.53;

molecular mass: found 1120; calculated 1046.

Surface tension of the 0.01 percent aqueous solution is 42 dynes/cm.

Critical concentration of micelle-formation is 0.0110 g/l.

The yield of hydroperoxide derivatives of 2,4-dinonylphenyloxydecaethylene oxide is quantitative relative to the isomers of acid 2-methyl-cis- Δ⁴-tetrahydrophthalate of 2,4-dinonylphenyloxydecaethylene oxide.

The hydroperoxide derivatives of 2,4-dinonylphenyloxydecaethylene oxide can be used for emulsion polymerization of styrene.

Polymerization of styrene is carried out as described in Example 1.

The yield of the polymer is quantitative in 1.8 hours. Molecular mass is 1,000,000.

The average size of the particles is 0.06 μ.

The resulting latex contains no coagulum and retains the aggregative stability for one year.

Hydroperoxide derivatives of 2,4-dinonylphenyloxydecaethylene oxide can also be used for emulsion polymerization of other vinyl monomers described in Example 1.

EXAMPLE 3

The experiment is carried out under conditions similar to those described in Example 1, except that polyethylene oxide-block-propylene oxide of the following structure

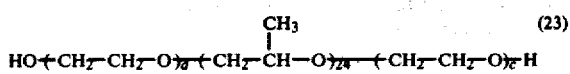

is substituted for octadecyloxyeicosyethylene oxide.

Molar ratios of the reagents are similar to those described in Example 1.

The acylate separated is substantially a mixture of the following two isomers

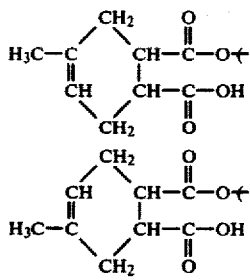

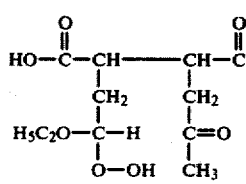

The presented structures are supported by the following data: acid number: found 55.3; calculated 55.9; elementary composition, percent: found H—9.6; C—60.7; calculated H—9.5; C—61.1.

IR-spectrum of the substance synthesized reveals absorption in the band of 1740 cm$^{-1}$, which is characteristic of carbonyl groups.

The yield of acylates relative to polyethylene oxide-block-propylene oxide is 60 percent.

Ozonization is carried out as in Example 1. Obtained is a mixture of isomers of hydroperoxide derivatives of poly/ethylene oxide-block-propylene oxide/, which are as follows.

1. Bis/2-formyl-methyl-3-carboxy-5-ethoxy-5-hydroperoxyhexanoyl/-α, ω-poly/ethylene oxide-block-propylene oxide/

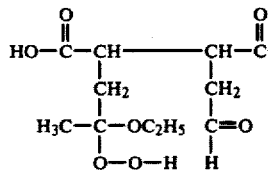 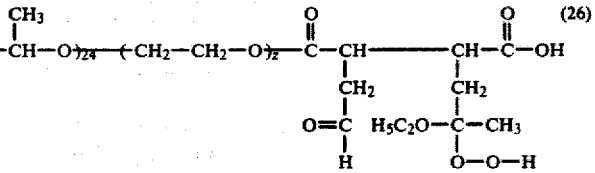

1. Bis 2-/2-ethoxy-2-hydroperoxy-ethyl/3-carboxy-5-oxohexanoyl/-α, ω-poly/ethylene oxide-block-propylene oxide/

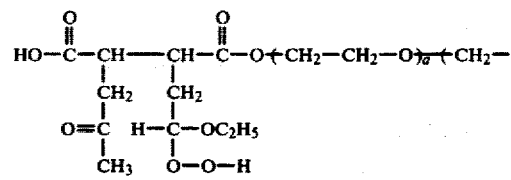 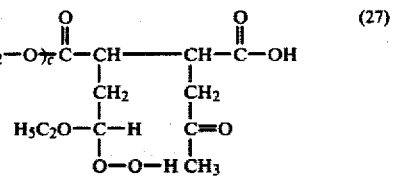

3. Bis/2-acetonyl-3-carboxy-5-ethoxy-5-hydroperoxy-pentanoyl/-α, ω-poly/ethylene oxide-block-propylene oxide/

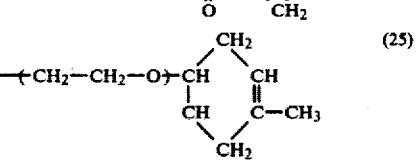 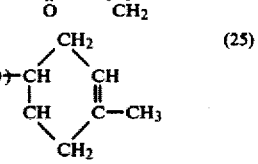

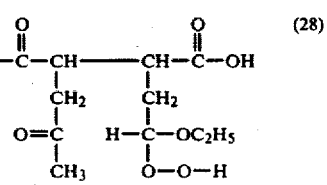

4. Bis 2-/2-ethoxy-2-hydroperoxypropyl/-3-carboxy-5-oxopentanoyl/-α, ω-poly/ethylene oxide-block-propylene oxide/

$$\underset{(29)}{\text{HO}-\overset{O}{\overset{\|}{C}}-\underset{\underset{H}{\overset{|}{O=C}}}{\overset{|}{\underset{|}{CH_2}}}-\underset{\underset{O-O-H}{\overset{|}{H_3C-\overset{|}{C}-OC_2H_5}}}{\overset{|}{\underset{|}{CH_2}}}\overset{O}{\overset{\|}{C}}-O(CH_2-CH_2-O)_a(CH_2-\overset{\overset{CH_3}{|}}{CH}-O)_{24}(CH_2-CH_2-O)-\overset{O}{\overset{\|}{C}}-\underset{\underset{O-O-H}{\overset{|}{H_5C_2O-\overset{|}{C}-CH_3}}}{\overset{|}{\underset{|}{CH_2}}}\underset{\underset{H}{\overset{|}{C=O}}}{\overset{|}{\underset{|}{CH_2}}}\overset{O}{\overset{\|}{C}}-\text{OH}}$$

The presented structures are supported by the following data:

elementary composition, percent: found H—9.2; C—58.2; calculated H—9.2; C—57.9;

active oxygen content, percent: found 1.49; calculated 1.46;

molecular mass: found 1900; calculated 2194.

Surface tension of the 0.01 percent aqueous solution is 49 dynes/cm.

Critical concentration of micelle-formation is 0.0090 g/l.

The yield of hydroperoxide derivatives of poly/ethylene oxide-block-propylene oxide/ relative to acid ester is quantitative.

The hydroperoxide derivatives of poly/ethylene oxide-block-propylene oxide/ can be used for emulsion polymerization of styrene.

Polymerization of styrene is carried out in a way similar to the process of Example 1.

The polymer yield is quantitative in 1.2 hours.

Molecular mass is 500,000. The average size of the particles is 0.03μ. The resulting latex contains no coagulum and retains its aggregative stability for one year.

The hydroperoxide derivatives of poly(ethylene oxide-block-propylene oxide) can also be used for emulsion polymerization of other vinyl monomers described in Example 1.

EXAMPLE 4

The experiment is carried out under conditions similar to those of Example 1 except that octyloxydecaethylene oxide is substituted for the octadecyloxyeicosaethylene oxide.

Molar ratios of the reagents are similar to those of Example 1.

The acylate separated is substantially a mixture of the following two isomers of acid octyloxydecaoxirane 4-methyl-cis-Δ⁴-tetrahydrophthalate:

$$(30)\quad H_3C-\underset{CH}{\overset{CH_2}{\diagdown}}\underset{\diagup}{\overset{\diagdown}{C}}\underset{CH_2}{\overset{CH-C+O-CH_2-CH_2)_{10}-O-C_8H_{17}}{\underset{|}{\underset{CH-C-OH}{}}}}$$

$$(31)\quad H_3C-\underset{C}{\overset{CH_2}{\diagdown}}\underset{\diagup}{\overset{\diagdown}{CH}}\underset{CH_3}{\overset{CH-C+O-CH_2-CH_2)_{10}-O-C_8H_{17}}{\underset{|}{\underset{CH-C-OH}{}}}}$$

The presented structures are supported by the following
data: acid number: found 76.8; calculated 76.1;
elementary composition, percent: found H 9.11; C 60.5; calculated H 9.24; C 60.3.

IR-spectrum of the substance synthesized shows absorption in the band of 1740 cm⁻¹, which is characteristic of carbonyl groups.

The yield of the isomers of acid octyloxydecaoxirane 4-methyl-cis-Δ⁴-tetrahydrophthalate is 70 percent (relative to octyloxy-decaethylene oxide).

Ozonization is carried out as in Example 1. Obtained is a mixture of four isomers of hydroperoxide derivatives of octyloxydecaethylene oxide.

1. 2-formyl-ethyl-3-carboxy-5-ethoxy-5-hydroperoxyhexanoyloctyloxy-decaethylene oxide $$(32)\quad HO-\overset{O}{\overset{\|}{C}}-\underset{\underset{O-O-H}{\overset{|}{H_3C-\overset{|}{C}-OC_2H_5}}}{\overset{|}{\underset{|}{CH_2}}}\underset{\underset{H}{\overset{|}{C=O}}}{\overset{|}{\underset{|}{CH_2}}}\overset{O}{\overset{\|}{C}}+O-CH_2-CH_2)_{10}-O-C_8H_{17}$$

2. 2-(2-ethoxy-2-hydroperoxyethyl)-3-carboxy-5-oxohexanoyloctyloxydecaethylene oxide $$(33)\quad HO-\overset{O}{\overset{\|}{C}}-\underset{\underset{CH_3}{\overset{|}{O=C}}}{\overset{|}{\underset{|}{CH_2}}}\underset{\underset{O-O-H}{\overset{|}{H-\overset{|}{C}-OC_2H_5}}}{\overset{|}{\underset{|}{CH_2}}}\overset{O}{\overset{\|}{C}}+O-CH_2-CH_2)_{10}-O-C_8H_{17}$$

3. 2-acetonyl-3-carboxy-5-ethoxy-5-hydroperoxypentanoyloctyloxydecaethylene oxide $$(34)\quad HO-\overset{O}{\overset{\|}{C}}-\underset{\underset{O-O-H}{\overset{|}{H_5C_2O-\overset{|}{C}-H}}}{\overset{|}{\underset{|}{CH_2}}}\underset{\underset{CH_3}{\overset{|}{C=O}}}{\overset{|}{\underset{|}{CH_2}}}\overset{O}{\overset{\|}{C}}+O-CH_2-CH_2)_{10}-O-C_8H_{17}$$

4. 2-(2-ethoxy-2-hydroperoxypropyl)-3-carboxy-5-oxopentanoyloxydecaethylene oxide $$(35)\quad HO-\overset{O}{\overset{\|}{C}}-\underset{\underset{H}{\overset{|}{O=C}}}{\overset{|}{\underset{|}{CH_2}}}\underset{\underset{O-O-H}{\overset{|}{H_3C-\overset{|}{C}-OC_2H_5}}}{\overset{|}{\underset{|}{CH_2}}}\overset{O}{\overset{\|}{C}}+O-CH_2-CH_2)_{10}-O-C_8H_{17}$$

The presented structures are supported by the following
data: elementary composition, percent: found H 9.09; C 56.8; calculated H 8.92; C 56.4;

active oxygen content, percent: found 2.02; calculated 1.93;

molecular mass: found 800; calculated 830.

Surface tension of the 0.01 percent aqueous solution i 42 dynes/cm.

Critical concentration of micelle-formation is 0.0085 g/l.

The yield of hydroperoxide derivatives of octyloxydecaethylene oxide is quantitative relative to the isomers of acid ocydecaoxirane 4-methyl-cis-$\Delta^4$-tetrahydrophthalate.

The hydroperoxide derivatives of octyloxydecaethylene oxide are used for emulsion polymerization of styrene.

Polymerization of styrene is carried out as described in Example 1, except that the temperature is 40° C. The polymer yield is quantitative in three hours. Molecular mass is 2,000,000. The average size of the particles is 0.10μ.

The resulting latex contains no coagulum and retains its aggregative stability for as long as one year.

Hydroperoxide derivatives of octyloxydecaethylene oxide can also be used in emulsion polymerization of other vinyl monomers described in Example 1.

EXAMPLE 5

The experiment is carried out under conditions similar to those of Example 1, except that eicosaloxytriacontaethylene oxide is substituted for the octadecyloxyeicosaethylene oxide.

The molar ratios of the reagents are analogous to those of Example 1.

The resulting acylate is substantially a mixture of the following two isomers of acid eicosaloxytriacontaoxirane 4-methyl-$\Delta^4$-tetrahydrophthalate.

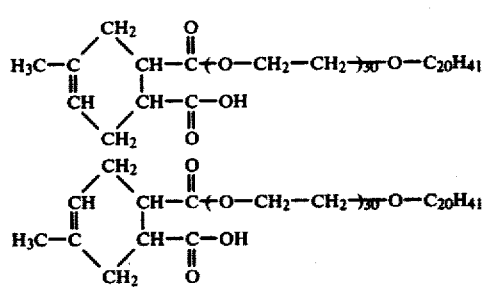

The presented structures are supported by the following data: acid number: found 31.9; calculated 31.4;

elementary composition, percent: found H—9.72; C—59.2; calculated H—9.64; C—59.8.

IR-spectrum of the substance synthesized shows absorption in the band of 1740 cm$^{-1}$, which is characteristic of carbonyl groups.

The yield of the isomers of acid eicosaloxytriacontaoxirane 4-methyl-cis-$\Delta^4$-tetrahydrophthalate is 68 percent (relative to the eicosyloxytriacontaethylene oxide).

Ozonization is carried out as in Example 1. Obtained is a mixture of four isomers of hydroperoxide derivatives of eicosaloxytriacontaethylene oxide, which are as follows.

1. 2-formyl-methyl-3-carboxy-5-ethoxy-5-hydroperoxyhexanoyl-eicosaloxytriacontaethylene oxide

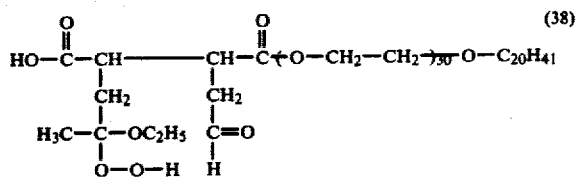

2. 2-ethoxyhydroperoxyethyl)-3-carboxy-5-oxohexanoyleicosaloxytriacontaethylene oxide

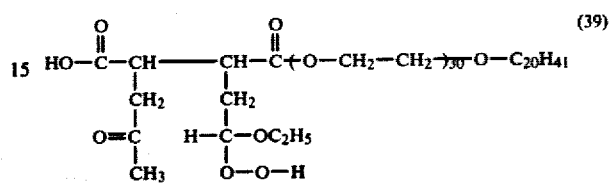

3. 2-acetonyl-3-carboxy-5-ethoxy-5-hydroperoxypentanoyleicosaloxytriacontaethylene oxide

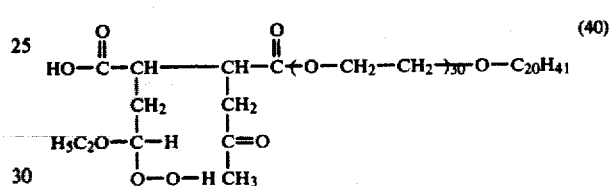

4. 2-(2-ethoxy-2-hydroperoxypropyl)-3-carboxy-3-oxopentanoyleicosaloxytriacontaethylene oxide

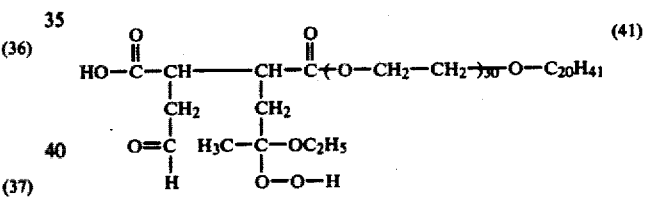

The presented structures are supported by the following data: elementary composition, percent: found H—9.29; C—59.1; calculated H—9.48; C—58.1;

active oxygen content, percent: found 0.91; calculated 0.85;

molecular mass: found 1770; calculated 1878.

Surface tension of the 0.01 percent aqueous solution is 40 dynes/cm.

Critical concentration of micelle-formation is 0.0043 g/l.

The yield of hydroperoxide derivatives of eicosaloxytriacontaethylene oxide is quantitative relative to the isomers of acid eicosaloxytriacontaoxirane 4-methyl-cis-$\Delta^4$-tetrahydrophthalate.

The hydroperoxide derivatives of eicosaloxytriacontaethylene oxide are used for emulsion polymerization of styrene.

Polymerization of styrene is carried out as described in Example 1.

The yield of the polymer is quantitative in 2.5 hours. Molecular mass is 1,500,000.

The average size of the latex particles is 0.08μ.

The resulting latex contains no coagulum and retains its aggregative stability for as long as one year.

The hydroperoxide derivatives of eicosaloxytriacontaethylene oxide can also be used in emulsion polymerization of other vinyl monomers described in Example 1.

EXAMPLE 6

The experiment is carried out under conditions similar to those of Example 1, except that poly(ethylene oxide-block-propylene oxide) of the following structure:

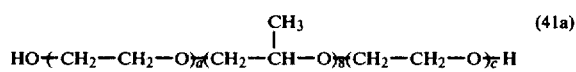

(41a)

wherein a+c=6 is substituted for octadecyloxyeicosaethylene oxide.

Molar ratios of the reagents are analogous to those of Example 1.

The acylate separated is substantially a mixture of the following two isomers

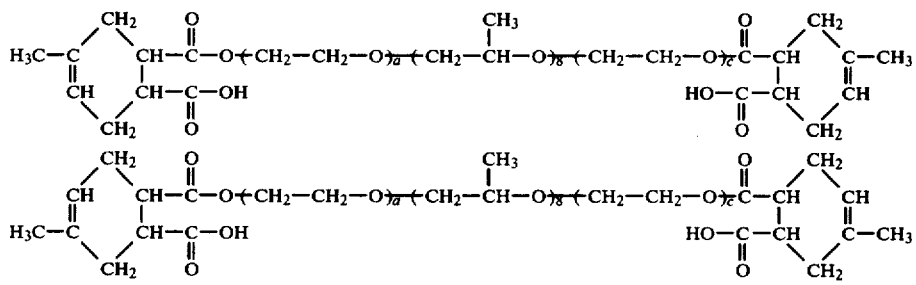

The presented structures are supported by the following data.

Acid number: found 53.1; calculated 52.6.

Elementary composition, percent: found H—8.79; C—57.3; calculated H—8.90; C—57.3.

IR-spectrum of the substance synthesized reveals absorption in the band of 1740 cm$^{-1}$, which is characteristic of carbonyl groups.

The yield of acylates relative to poly(ethylene oxide-block-propylene oxide) is 69 percent.

Ozonization is carried out as in Example 1. Obtained is a mixture of isomers of hydroperoxide derivatives of poly(ethylene oxide-block-propylene oxide), which are as follows.

1. Bis (2-formyl-methyl-3-carboxy-5-ethoxy-5-hydroperoxyhexanoyl)-α, ω-poly(ethylene oxide-block-propylene oxide).

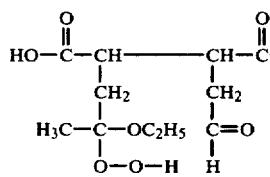
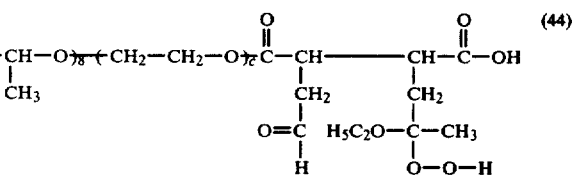

(44)

2. Bis 2-(2-ethoxy-2-hydroperoxy-ethyl)-3-carboxy-5-oxohexanoyl-α, ω-poly(ethylene oxide-block-propylene oxide)

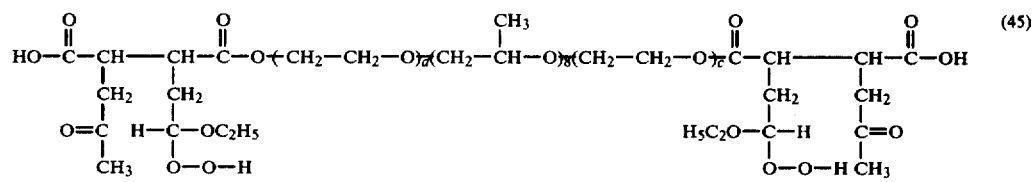

(45)

3. Bis (2-acetonyl-3-carboxy-5-ethoxy-5-hydroperoxypentanoyl)-α, ω-poly(ethylene oxide-block-propylene oxide).

(42)

(43)

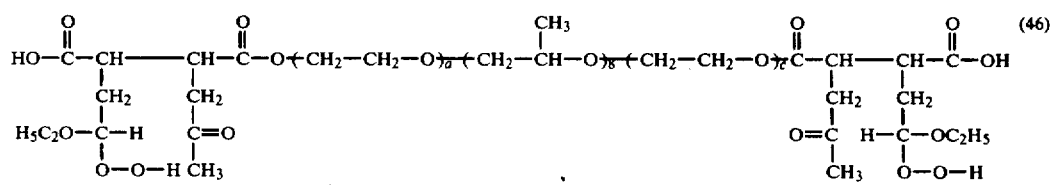

(46)

4. Bis 2-(2-ethoxy-2-hydroperoxy-propyl)-3-carboxy-5-oxopentanoyl-α, ω-poly(ethylene oxide-block-propylene oxide)

$$\underset{\text{(47)}}{\text{HO}-\overset{\text{O}}{\overset{\|}{\text{C}}}-\text{CH}-\underset{\underset{\text{H}}{\overset{|}{\text{O}=\text{C}}}}{\overset{|}{\underset{|}{\text{CH}_2}}}-\text{CH}-\overset{\text{O}}{\overset{\|}{\text{C}}}-\text{O}+\text{CH}_2-\text{CH}_2-\text{O})_{\overline{n}}(\text{CH}_2-\overset{\overset{\text{CH}_3}{|}}{\text{CH}}-\text{O})_{\overline{m}}(\text{CH}_2-\text{CH}_2-\text{O})_{\overline{k}}\overset{\text{O}}{\overset{\|}{\text{C}}}-\text{CH}-\underset{\underset{\text{O}-\text{O}-\text{H}}{\overset{|}{\text{H}_5\text{C}_2\text{O}-\overset{|}{\text{C}}-\text{CH}_3}}}{\overset{|}{\underset{|}{\text{CH}_2}}}-\text{CH}-\overset{\text{O}}{\overset{\|}{\text{C}}}-\text{OH}}$$

The presented structures are supported by the following data.

Elementary composition, percent: found H—8.74; C—54.3; calculated H—8.70; C—54.8.

Active oxygen content, percent: found 1.45; calculated 1.38.

Molecular mass: found 2080; calculated 2322.

Surface tension of the 0.01 percent aqueous solution is 50 dynes/cm.

Critical concentration of micelle-formation is 0.0055 g/l. The yield of hydroperoxide derivatives of poly-(ethylene oxide-block-propylene oxide) is quantitative relative to acid ester.

The hydroperoxide derivatives of poly(ethylene oxide-block-propylene oxide) are used for emulsion polymerization of styrene.

Polymerization of styrene is carried out as in Example 1, except that pH is 5.

The yield of the polymer is quantitative in two hours. Molecular mass is 1,400,000.

The average size of the latex particles is $0.07\mu$.

The resulting latex contains no coagulum and retains its aggregative stability when stored for as long as one year.

The hydroperoxide derivatives of poly(ethylene oxide-block-propylene oxide) can also be used for emulsion polymerization of other vinyl monomers described in Example 1.

EXAMPLE 7

The experiment is carried out under conditions similar to those of Example 1, except that 2,4-dioctyl-phenyloxydeaethylene oxide is substituted for octadecyloxyeicosaethylene oxide, and cis-$\Delta^4$-tetrahydrophthalic anhydride is substituted for 4-methyl-cis-$\Delta^4$-tetrahydrophthalic anhydride.

Molar ratio of the reagents is the same as in Example 1.

The acylate separated in substantially acid 2,4-dioctylphenyloxydecaoxirane cis-$\Delta^4$-tetrahydrophthalate:

(48)

The presented structure is supported by the following characteristics.

Acid number: found 61.3; calculated 61.5.

Elementary composition, percent: found H—9.4; C—65.8; calculated H—9.5; C—65.8.

In IR-spectrum of the substance synthesized shows absorption in the band of 1740 cm$^{-1}$, which is characteristic of carbonyl groups.

The yield of acylate is 78 percent relative to 2,4-dioctyl-phenyloxydecaethylene oxide.

Ozonization is carried out as in Example 1.

Obtained is a mixture of the following two isomers of hydroperoxide derivatives of 2,4 dioctylphenyloxydecaethylene oxide.

1. 2-formyl-methyl-3-carboxy-5-ethoxy-5-hydroperoxypentanoyl-2,4-dioctylphenyloxydecaethylene oxide.

(49)

2. 2(2-ethoxy-2-hydroperoxyethyl)-3-carboxy-5-oxo-pentanoyl-2,4-dioctylphenyloxydecaethylene oxide.

(50)

The presented structures of the compounds are supported by the following data.

Elementary composition, percent: found H—9.3; C—62.0; calculated H—9.2; C—62.1.

Active oxygen content: found 1.56; calculated 1.59.

Molecular mass: found 1050; calculated 1004.

Surface tension of the 0.01 percent aqueous solution is 40 dynes/cm.

Critical concentration of micelle-formation is 0.013 g/l.

The yield of hydroperoxide derivatives of 2,4-dioctylphenyloxydecaethylene oxide is quantitative relative to acid 2,4-dioctylphenyloxydecaoxirane cis $\Delta^4$-tetrahydrophthalate.

The hydroperoxide derivatives of 2,4-dioctyl-phenyloxydecaethylene oxide are used for emulsion polymerization of styrene.

Polymerization of styrene is carried out as described in Example 1, except that pH is 5.

Yield of the polymer is quantitative in 1.5 hours. Molecular mass is 800,000.

The average size of the particles is $0.05\mu$.

The resulting latex contains no coagulum and retains its aggregative stability when stored for as long as a year.

The hydroperoxide derivatives of 2,4-dioctyl-phenyloxydecaethylene oxide can also be used in emulsion polymerization of other vinyl monomers described in Example 1.

EXAMPLE 8

The experiment is carried out under conditions similar to those described in Example 1 except that 2,4- didodecylphenyloxydecaethylene oxide and 4,5-dimethyl-cis-$\Delta^4$-tetrahydrophthalic anhydride are substituted for the octadecyloxyeicosaethylene oxide and 4-methyl-cis-$\Delta^2$-tetrahydrophthalic anhydride, respectively.

Molar ratio of the reagents is the same as in Example 1.

The acylate separated is substantially acid 2,4-didodecylphenyloxydecaoxirane 4,5 dimethyl-cis-$\Delta^4$-tetrahydrophthalate.

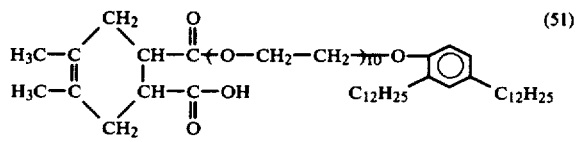
(51)

The presented structure is supported by the following characteristics.

Acid number: found 53.5; calculated 53.4.

Elementary composition, percent: found H 10.2; C 68.2; calculated H 10.1; C 68.5.

IR-spectrum of the substance synthesized shows absorption in the band of 1740 cm$^{-1}$, which is characteristic of carbonyl groups.

The acylate yield is 73 percent relative to 2,4-didodecylphenyloxydecaethylene oxide.

Ozonization is carried out as in Example 1.

Obtained is a mixture of the following two isomers of hydroperoxide derivatives of 2,4-didodecylphenyloxydecaethylene oxide.

1. 2-acetonyl-3-carboxy-5-ethoxyhydroperoxyhexanoyl-2,4-didodecylphenyldecaethylene oxide.

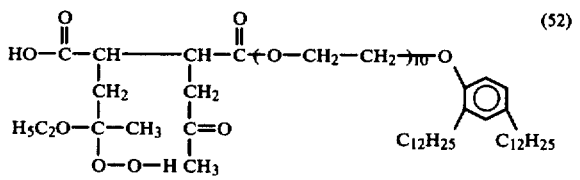
(52)

2. 2-(2-ethoxy-2-hydroperoxypropyl)-3-carboxy-5-oxohexanoyl-2,4-didodecylphenyloxydecaethylene oxide.

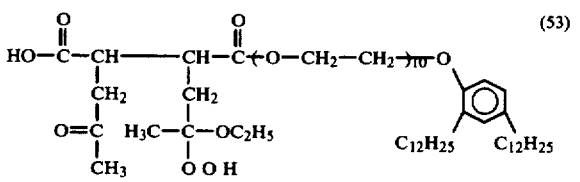
(53)

The presented structures of the compounds are supported by the following data:

elementary composition, percent: found H—10.0; C—65.2; calculated H—9.8; C—65.0;

active oxygen content: found 1.35; calculated 1.40;

molecular mass: found 1075; calculated 1144.

Surface tension of the 0.01 percent aqueous solution is 44 dynes/cm.

Critical concentration of derivatives of 2,4-didodecylphenyloxydecaethylene oxide is quantitative relative to acid 2,4-didodecylphenyloxydecaoxirane 4,5-dimethyl-cis-$\Delta^4$-tetrahydrophthalate.

The hydroperoxide derivatives of 2,4-didodecylphenyloxydecaethylene oxide are used for emulsion polymerization of styrene. Polymerization of styrene is carried out in the same way as in Example 1.

The yield of the polymer is quantitative in 1.5 hours. Molecular mass is 900,000.

The average size of the particles is 0.05$\mu$.

The resulting latex contains no coagulum and retains its aggregative stability when stored for at least a year.

The hydroperoxide derivatives of 2,4-didodecylphenyloxydecaethylene oxide can also be used for emulsion polymerization of other vinyl monomers described in Example 1.

EXAMPLE 9

The experiment is carried out under conditions analogous to those of Example 1, except that dodecyloiloxydecaethylene oxide and 3-methyl-cis-$\Delta^4$-tetrahydrophthalic anhydride are substituted for the octadecyloxyeicosathylene oxide and 4-methyl-cis-$\Delta^4$-tetrahydrophthalic anhydride, respectively.

Molar ratio of the reagents is analogous to that of Example 1.

The acylate separated is substantially a mixture of the following two isomers of acid dodecyloiloxydecaoxirane 3-methyl-cis-$\Delta^4$-tetrahydrophthalate.

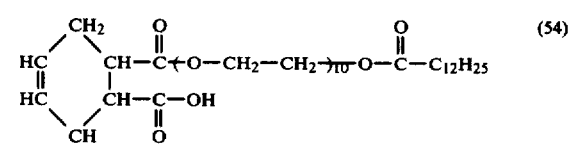
(54)

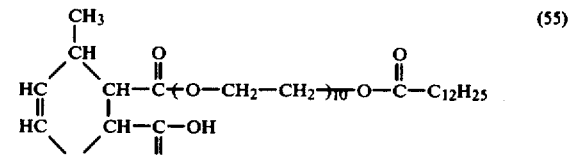
(55)

The presented structure is supported by the following characteristics.

Acid number: found 68.0; calculated 68.3.

Elementary composition: found H 8.5; C 61.3; calculated H 8.9; C 61.5

IR-spectrum of the substance synthesized shows increased intensity of the absorption band in the band of 1740 cm$^{-1}$ characteristic of carbonyl groups.

Yield of the acylate is 80 percent relative to dodecyloiloxydecaethylene oxide.

Ozonization is carried out as in Example 1.

Obtained is a mixture of four isomers of hydroperoxide derivatives of dodecyloiloxydecaethylene oxide.

1. 2-(2-formyl-ethyl)-3 carboxy-5 ethoxy-5-hydroperoxypentanoyldodecyloiloxydecaethylene oxide.

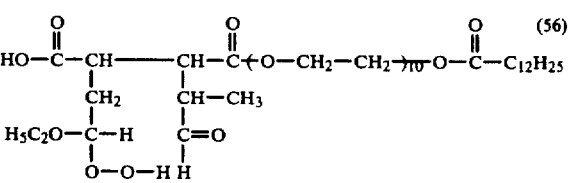
(56)

2. 2-(1-methyl-2-ethoxy-2-hydroperoxyethyl)-3-carboxy-5-oxopentanoyldodecyloyloxydecaethylene oxide.

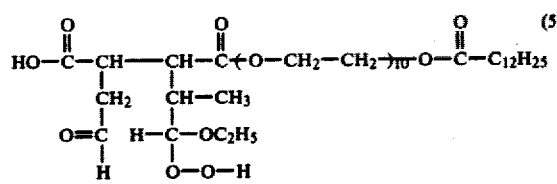
(57)

3. 2-formyl-methyl-3-carboxy-4-methyl-5-ethoxy-5-hydroperoxypentanoyl dodecyloyloxydecaethylene oxide

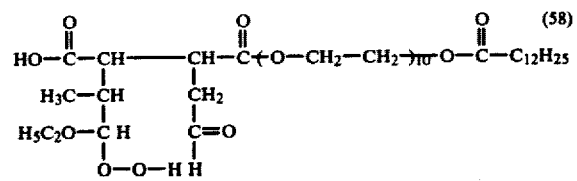
(58)

4. 2(2-ethoxy-2-hydroperoxy-ethyl)-3-carboxy-4-methyl-5-oxopentanoyl dodecyloyloxydecaethylene oxide.

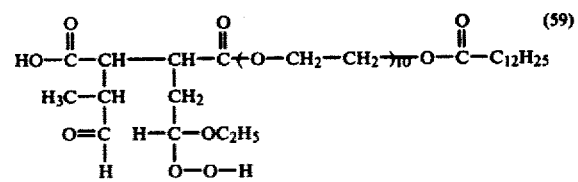
(59)

The presented structures of the compounds are supported by the following data.

Elementary composition, percent: found H—8.4; C—57.1; calculated H—8.7; C—57.8.

Active oxygen content: found 1.72; calculated 1.75.

Surface tension of the 0.01 percent aqueous solution is 39 dynes/cm.

Critical concentration of micelle-formation is 0.008 g/l.

Molecular mass: found 890; calculated 914.

The yield of hydroperoxide derivatives of dodecyloyloxydecaethylene oxide is quantitative relative to acid dodecyloiloxydecaoxirane 3-methyl-cis-Δ4-tetrahydrophthalate.

The hydroperoxide derivatives of dodecyloyloxydecaethylene oxide are used for emulsion polymerization of styrene.

Polymerization is carried out as described in Example 1, except that the temperature is 80° C.

The yield of the polymer is quantitative in 1.3 hours. Molecular mass is 800,000.

The average size of the particles is 0.05μ.

The resulting latex contains no coagulum and retains its aggregative stability when stored for as long as year.

The hydroperoxide derivatives of dodecyloyloxydecaethylene oxide can also be used in emulsion polymerization of other vinyl monomers described in Example 1.

EXAMPLE 10

The experiment is carried out under conditions similar to those of Example 1, except that nonadecanoic acid amide-N-(eicosaethylene oxide) and bicyclo [2,2,1]heptΔ5-en-2,3-dicarboxylic acid anhydride are substituted for octadecyloxyeicosaethylene oxide and 4-methyl-cis-Δ4-tetra-hydrophthalic anhydride.

Molar ratio of the reagents is similar to that of Example 1.

The acylate separated is substantially acid ester of nonadecanoic acid amide-N-(eicosaethylene oxide) and bicyclo [2,2,1] hept-Δ5-en-2,3-dicarboxylic acid anhydride.

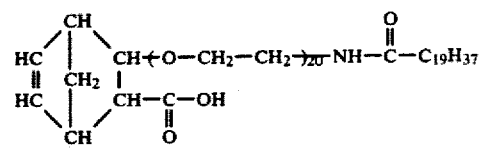

The presented structure is supported by the following characteristics.

Acid number: found 41.0; calculated 41.4.

Elementary composition, percent: found H 9.1; C 60.6; calculated H 9.4; C 60.3.

IR-spectrum of the substance synthesized shows absorption in the band of 1740 cm$^{-1}$, which is characteristic of carbonyl groups.

The yield of acylate is 75 percent relative to nonadecanoic acid amide-N-(eicosaethylene oxide).

Ozonization is carried out as in Example 1.

Obtained is a mixture of the following two isomers of hydroperoxide derivatives of nonadecanoic acid amide-N-(eicosaethylene oxide).

1. Nonadecanoic acid amide-N-(eicosyethylene oxide) and 2-carboxy-3-ethoxy, hydroperoxy-methyl-5-formyl cyclopentane carbonate.

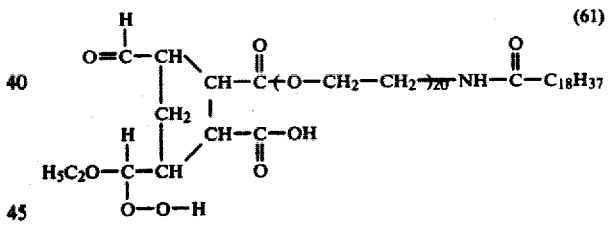
(61)

2. Nonadecanoic acid amide-N-(eicosaethylene oxide)-2-carboxy-3formyl-5(ethoxy, hydroperoxy-methyl) cyclopentane carbonate

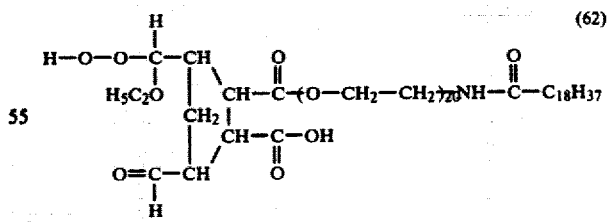
(62)

The presented structures of the compounds are supported by the following data.

Elementary composition, percent: found H 9.3; C 57.4; calculated H 9.3; C 58.5.

Active oxygen content: found 1.05; calculated 1.10.

Molecular mass: found 1389; calculated 1435.

Surface tension of the 0.01 percent aqueous solution is 48 dynes/cm.

Critical concentration of micelle-formation is 0.03 g/l.

The yield of hydroperoxide derivatives of nonadecanoic acid amide-N-(eicosaethylene-oxide) is quantitative relative to the acid ester.

The hydroperoxide derivatives of nonadecanoic acid-N-(eicosaethylene oxide) are used for emulsion polymerization of styrene.

Polymerization is carried out in the same way as in Example 1.

The yield of the polymer is quantitative in two hours. Molecular mass is 1,500,000.

The average size of the particles is 0.07μ.

The resulting latex contains no coagulum and retains its aggregative stability when stored for as long as a year.

The hydroperoxide derivatives of nonadecanoic acid amide-N-(eicosaethylene oxide) can also be used for emulsion polymerization of other vinyl monomers described in Example 1.

EXAMPLE 11.

The experiment is carried out under conditions similar to those of Example 1, except that a mixture of secondary isomers of tetra-decyloxyeicosaethylene oxide and pentadecyloxyeicosaethylene oxide, and cis-$\Delta^4$-tetrahydrophthalic anhydride are substituted for octadecyloxyeicosaethylene oxide and 4-methyl-cis-$\Delta^4$-tetrahydrophthalic anhydride, respectively.

Molar ratio of the reagents is the same as in Example 1.

The acylate separated is substantially a mixture of acid cis-$\Delta^4$-tetrahydrophthalates of secondary isomers of tetradecyloxyeicosaethylene oxide and pentadecyloxyeicosyethylene oxide.

$$\begin{array}{c} \text{CH}_2 \\ \text{HC} \diagup \diagdown \text{CH}-\overset{\text{O}}{\overset{\|}{\text{C}}}-(\text{O}-\text{CH}_2-\text{CH}_2)_{20}\text{O}-\text{C}_{14-15}\text{H}_{29-31} \\ \overset{\|}{\text{HC}} \quad | \\ \diagdown \diagup \text{CH}-\text{C}-\text{OH} \\ \text{CH}_2 \quad \overset{\|}{\text{O}} \end{array} \quad (63)$$

The presented structure is supported by the following characteristics.

Acid number: found 44.2; calculated 44.6.

Elementary composition, percent: found H—9.1; C—59.5; calculated H—9.5; C—59.8.

In IR-spectrum of the substance synthesized reveals absorption in the band of 1740 cm$^{-1}$, which is characteristic of carbonyl groups.

The yield of the acylate is 78 percent relative to the mixture of secondary isomers of tetradecyloxyeicosyethylene oxide and pentadecyloxyeicosaethylene oxide.

Ozonization is carried out as in Example 1.

Obtained is a mixture of secondary isomers of hydroperoxidic derivatives of tetradecyloxyeicosaethylene oxide and pentadecyloxyeicosaethylene oxide, which are as follows.

1. Mixture of secondary isomers of 2-formylmethyl-3-carboxy-5-ethoxy-5-hydroperoxypentanoyl-tetradecyloxyeicosaethylene oxide and 2-formylmethyl-3-carboxy-5-ethoxy-5-hydroperoxypentanoyl pentadecyloxyeicosaethylene oxide $$\begin{array}{c} \overset{\text{O}}{\overset{\|}{\text{HO}-\text{C}}}-\text{CH}-\!\!\text{CH}-\overset{\text{O}}{\overset{\|}{\text{C}}}-(\text{O}-\text{CH}_2-\text{CH}_2)_{20}\text{O}-\text{C}_{14-15}\text{H}_{29-31} \\ |\quad\quad\quad| \\ \text{CH}_2\quad \text{CH}_2 \\ |\quad\quad\quad| \\ \text{H}_5\text{C}_2\text{O}-\text{C}-\text{H}\quad \text{C}=\text{O} \\ |\quad\quad\quad| \\ \text{O}-\text{O}-\text{H}\quad \text{H} \end{array} \quad (64)$$

2. Mixture of secondary isomers of 2(2-ethoxy-2-hydroperoxyethyl)-3-carboxy-5-oxopentanoyl-tetradecyloxyeicosaethylene oxide and 2(2-ethoxy-2-hydroperoxyethyl)-3-carboxy-5-oxopentanoyl pentadecyloxyeicosaethylene oxide $$\begin{array}{c} \overset{\text{O}}{\overset{\|}{\text{HO}-\text{C}}}-\text{CH}-\!\!\text{CH}-\overset{\text{O}}{\overset{\|}{\text{C}}}-(\text{O}-\text{CH}_2-\text{CH}_2)_{20}\text{O}-\text{C}_{14-15}\text{H}_{28-31} \\ |\quad\quad\quad| \\ \text{CH}_2\quad \text{CH}_2 \\ |\quad\quad\quad| \\ \text{O}=\text{C}\quad \text{H}-\text{C}-\text{OC}_2\text{H}_5 \\ |\quad\quad\quad| \\ \text{H}\quad\quad \text{O}-\text{O}-\text{H} \end{array} \quad (65)$$

The present structures of the compounds are supported by the following data.

Elementary composition, percent: found H—9.5; C—57.0; calculated H—9.3; C—57.5.

Active oxygen content, percent: found 1.15; calculated 1.13.

Molecular mass: found 1290; calculated 1347.

Surface tension of the aqueous solution is 45 dynes/cm.

Critical concentration of micelle-formation is 0.0070 g/l.

The yield of hydroperoxide derivatives of the mixture of secondary isomers of tetradecyloxyeicosaethylene oxide and pentadecyloxyeicosaethylene oxide is quantitative relative to the mixture of secondary isomers of tetradecyloxyeicosaethylene oxide and pentadecyloxyeicosaethylene oxide.

The hydroperoxide derivatives of the mixture of secondary isomers of tetradecyloxyeicosaethylene oxide and pentadecyloxyeicosaethylene oxide are used for emulsion polymerization of styrene.

Polymerization of styrene is carried out as in Example 1, except that the pH is 10.

The yield of the polymer is quantitative in 1.8 hours. Molecular mass is 1,000,000.

The average size of the particles is 0.06μ.

The resulting latex contains no coagulum and retains its aggregative stability when stored for as long as a year.

The hydroperoxide derivatives of the mixture of secondary isomers of tetradecyloxyeicosaethylene oxide and pentadecyloxyeicosaethylene oxide can also be used for emulsion polymerization of other vinyl monomers described in Example 1.

Example 12.

The experiment is carried out under conditions analogous to those of Example 1, except that cis-$\Delta^4$-tetrahydrophthalic anhydride is substituted for 4-methyl-cis-$\Delta^4$-tetrahydrophthalic anhydride.

Molar ratio of the reagents is the same as in Example 1.

The acylate separated is substantially acid octadecyloxyeicosaoxinane cis-$\Delta^4$-tetrahydrophthalate.

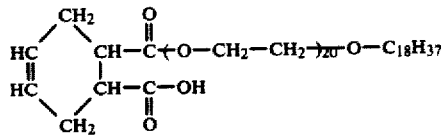

The presented structure is supported by the following characteristics.

Acid number: found 42.5; calculated 43.0.

Elementary composition, percent: found H—9.5; C—60.2; calculated H—9.7; C—60.7.

IR-spectrum of the substance synthesized shows absorption in the band of 1740 cm$^{-1}$, which is characteristic of carbonyl groups.

The acylate yield is 70 percent relative to the octadecyloxyeicosaethylene oxide.

Ozonization is carried out as in Example 1, except that methyl alcohol is substituted for the ethyl alcohol.

Obtained is a mixture of the following two isomers of hydroperoxide derivatives of octadecyloxyeicosaethylene oxide.

1. 2-formylmethyl-3-carboxy-5-methoxy-5-hydroperoxypentanoyloctadecyloxyeicosaethylene oxide

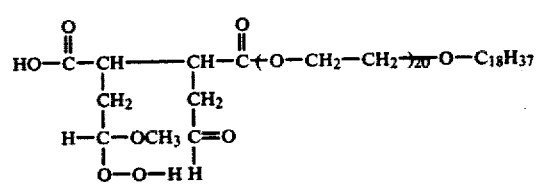

2. 2(2-methoxy-2-hydroperoxy)ethyl-3-carboxy-5-oxopentanoyloctadecyloxyeicosaethylene oxide

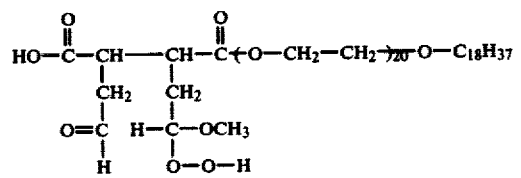

The presented structures are supported by the following characteristics.

Elementary composition, percent: found H—9.1; C—58.3; calculated H—9.4; C—58.0.

Active oxygen content, percent: found 1.07; calculated 1.15.

Molecular mass: found 1300; calculated 1382.

Surface tension 44 dynes/cm.

Critical concentration of micelle-formation 0.0060 g/l.

The yield of hydroperoxide derivatives of octadecyloxyeicosaethylene oxide is quantitative relative to the acid ester.

The hydroperoxide derivatives of octadecyloxyeicosa ethylene oxide are used for emulsion polymerization of styrene. Polymerization is carried out in the same way as in Example 1. The polymer yield is quantitative in two hours. Molecular mass is 1,200,000. The average size of the particle is 0.07μ. The resulting latex contains no coagulum and retains its aggregative stability when stored for at least an year.

The hydroperoxidic derivatives of octadecyloxyeicosaethylene oxide can also be used for emulsion polymerization of other vinyl monomers described in Example 1.

Example 13.

The experiment is carried out under conditions similar to those of Example 1, except that cis-Δ$^4$-tetrahydrophthalic anhydride is substituted for the 4-methyl-cis-Δ$^4$-tetrahydrophthalic anhydride.

Molar ratio of the reagents is the same as in Example 1.

The acylate which is substantially acid octadecyloxyeicosaoxiraneoxizane cis-Δ$^4$-tetrahydrophthalate has been illustrated in Example 12.

Ozonization is carried out in a medium of chloroform in the presence of nonyl alcohol. Conditions of ozonization are the same as shown in Example 1. The molar ratio of chloroform to nonyl alcohol to acid ester is 5:1:1.

Obtained is a mixture of the following two isomers of hydroperoxide derivatives of octadecyloxyeicosaethylene oxide.

1. 2-formyl-methyl-3-carboxy-5-oxynonyl-5-hydroperoxypentanoyloctadecyloxyeicosyethylene oxide

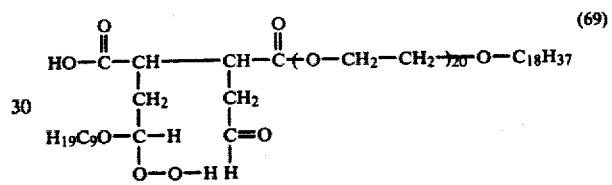

2. 2(2-oxynonyl-2-hydroperoxyethyl)-3-carboxy-5-oxopentanoyloctadecyloxyeicosaethylene oxide

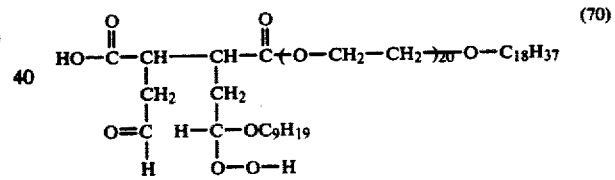

The presented structures are supported by the following characteristics.

Elementary composition, percent: found H—9.5; C—60.0; calculated H—9.8; C—60.2.

Active oxygen content, percent: found 1.03; calculated 1.07.

Molecular mass: found 1450; calculated 1494.

Surface tension 42 dynes/cm.

Critical concentration of micelle-formation 0.005 g/l.

The yield of hydroperoxide derivatives is quantitative relative to the acid ester.

The hydroperoxide derivatives of octadecyloxyeicosaethylene oxide are used for emulsion polymerization of styrene.

Polymerization is carried out in the same way as shown in Example 1, except that pH is 11.

The polymer yield is quantitative within 1.5 hours.

Molecular mass is 850,000.

The average size of the particles is 0.05μ.

The resulting latex contains no coagulum and retains its aggregative stability for a year.

The hydroperoxide derivatives of octadecyloxyeicosaethylene oxide can also be used in emulsion

We claim:

1. Hydroperoxide derivatives of hydroxyethylated compounds of the general formula:

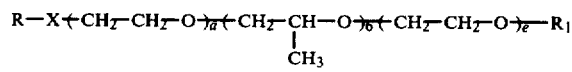

with x selected from the group consisting of

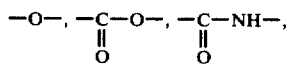

a—whole number selected from the range from 10 to 30, b is absent, c is absent,

R is selected from the group of normal alkyls from $C_8$ to $C_{20}$ secondary alkyls $C_{14}$, $C_{15}$,

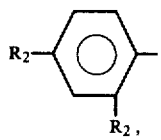

where $R_2$ is selected from the group of normal alkyls of $C_8$ to $C_{12}$, where

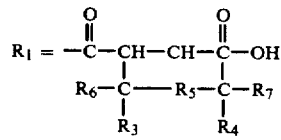

where
$R_3$ and $R_4$ are selected from the group consisting of

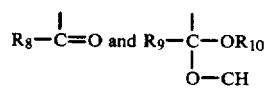

when $R_3 \neq R_4$,
where $R_8$ is selected from the group consisting of —$CH_3$ and H with $R_{6,7,9}$=H,$R_5$ is absent,
$R_9$ is selected from the group consisting of —$CH_3$ and H with $R_{6,7,8}$=H,$R_5$ is absent,
$R_{10}$ is selected from the group of normal alkyls from $C_1$ to $C_9$; $R_5$=—$CH_2$- if $R_{6,7,8,9}$=H, if $R_5$ is absent, $R_1$ is acyclic and is

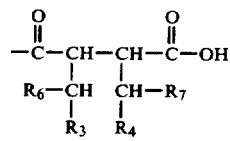

$R_6$ is selected from the group consisting of —$CH_3$ and H with $R_{7,8,9}$=H, $R_5$ is absent,
$R_7$ is selected from the group consisting of —$CH_3$ and H with $R_{6,8,9}$=H, $R_5$ is absent;
with x=—O—, b—whole number selected from the range from 8 to 24, the total of (a+c) is a whole number selected from the range of 6 to 30

$R = R_1$

2. Hydroperoxide derivatives of claim 1, wherein x is —O—.

3. Hydroperoxide derivatives of claim 1, wherein x is

4. Hydroperoxide derivatives of claim 1, wherein x is

5. Hydroperoxide derivatives of claim 1, wherein R is $C_8$-$C_{20}$ normal alkyl.

6. Hydroperoxide derivatives of claim 1, wherein R is a secondary alkyl of $C_{14}$ or $C_{15}$.

7. Hydroperoxide derivatives of claim 1, wherein R is

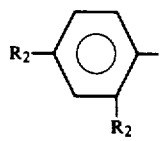

where $R_2$ is selected from the group consisting of $C_8$-$C_{12}$ normal alkyls.

8. Hydroperoxide derivatives of claim 1, wherein $R_5$ is absent.

* * * * *